(12) United States Patent
Crampton

(10) Patent No.: US 8,981,132 B2
(45) Date of Patent: *Mar. 17, 2015

(54) PRETREATED EPOXIDATION CATALYST AND A PROCESS FOR PRODUCING AN OLEFIN THEREWITH

(71) Applicant: Dow Global Technologies LLC, Midland, MI (US)

(72) Inventor: Hannah L. Crampton, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/252,149

(22) Filed: Apr. 14, 2014

(65) Prior Publication Data
US 2014/0243538 A1    Aug. 28, 2014

Related U.S. Application Data

(62) Division of application No. 13/636,706, filed as application No. PCT/US2011/000521 on Mar. 22, 2011, now Pat. No. 8,735,612.

(60) Provisional application No. 61/317,383, filed on Mar. 25, 2010.

(51) Int. Cl.
| | | |
|---|---|---|
| *C07D 303/00* | (2006.01) | |
| *C07D 303/08* | (2006.01) | |
| *B01J 29/89* | (2006.01) | |
| *B01J 37/02* | (2006.01) | |
| *B01J 37/06* | (2006.01) | |
| *B01J 38/52* | (2006.01) | |
| *C07D 301/12* | (2006.01) | |

(52) U.S. Cl.
CPC ............ *C07D 303/08* (2013.01); *B01J 29/89* (2013.01); *B01J 37/0203* (2013.01); *B01J 37/0209* (2013.01); *B01J 37/06* (2013.01); *B01J 38/52* (2013.01); *C07D 301/12* (2013.01)
USPC .......................................................... 549/512

(58) Field of Classification Search
CPC ..................................................... C07D 301/12
USPC ........................................................... 549/512
See application file for complete search history.

(56) References Cited

U.S. PATENT DOCUMENTS

| | | |
|---|---|---|
| 4,410,501 A | 10/1983 | Taramasso et al. |
| 4,833,260 A | 5/1989 | Neri et al. |
| 6,169,050 B1 | 1/2001 | Catinat et al. |
| 6,821,923 B1 | 11/2004 | Kuperman et al. |
| 7,323,578 B2 | 1/2008 | Catinat et al. |
| 2005/0277542 A1 | 12/2005 | Kaminsky et al. |

FOREIGN PATENT DOCUMENTS

CN    200710039080    10/2008

OTHER PUBLICATIONS

International Search Report and Written Opinion from related PCT application PCT/US2011/000521, dated Jun. 29, 2011, 13 pages.
International Preliminary Report on Patentability from related PCT application PCT/US2011/000521, dated Jun. 11, 2012, 17 pages.

*Primary Examiner* — Nizal Chandrakumar
(74) *Attorney, Agent, or Firm* — Brooks, Cameron & Huebsch, PLLC

(57) ABSTRACT

A pretreated titanium silicalite with MFI structure (TS-1) catalyst which has been pretreated with methanol, and then optionally filtered and optionally air-dried to form a pretreated activated TS-1 catalyst. The activated TS-1 may be used in an epoxidation reaction with no additional methanol added and has equivalent activity to TS-1 used with large excesses of methanol. By removing the need for additional methanol during the reaction, the losses of epichlorohydrin from solvolysis are minimized significantly.

4 Claims, 1 Drawing Sheet

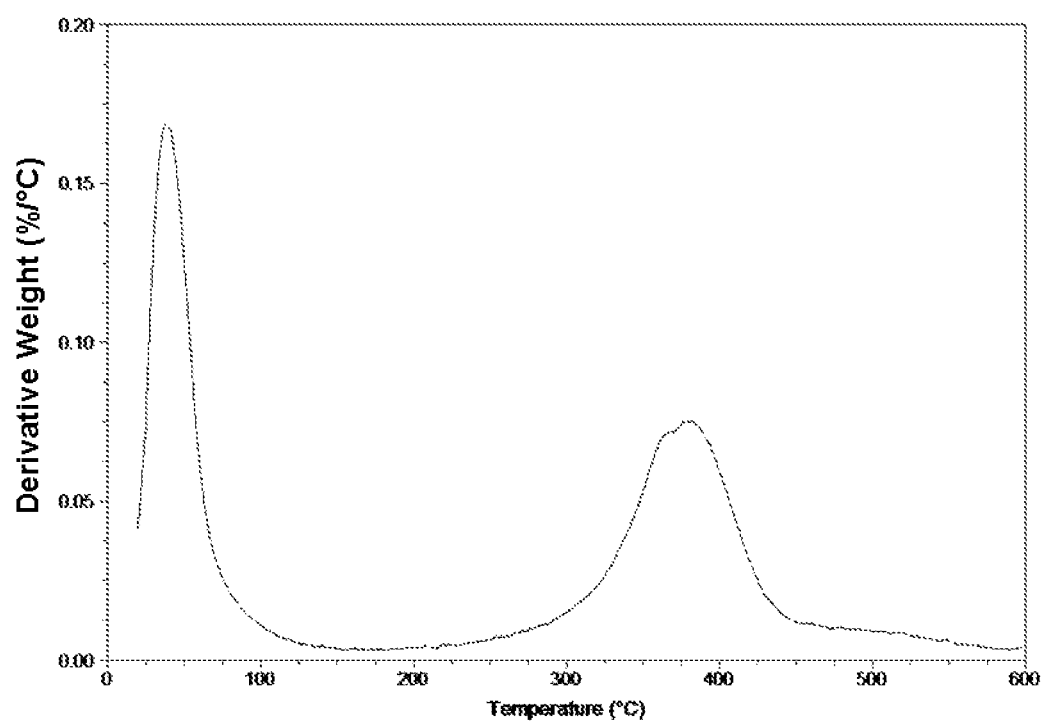

PRETREATED EPOXIDATION CATALYST AND A PROCESS FOR PRODUCING AN OLEFIN THEREWITH

CLAIM OF PRIORITY

This Application is a Divisional Application of U.S. National Stage application Ser. No. 13/636,706, filed Sep. 24, 2012 and published as U.S. Publication No. 2013/0012731 on Jan. 10, 2013, which claims the benefit to International Application Number PCT/US2011/000521, filed Mar. 22, 2011 and published as WO 2011/119215 on Sep. 29, 2011, which claims the benefit to U.S. Provisional Application 61/317,383, filed Mar. 25, 2010, the entire contents of which are incorporated herein by reference in its entirety.

BACKGROUND OF THE INVENTION

1. Field of the Invention

The present invention relates to catalysts for use in chemical reactions. More specifically, the present invention relates to a pretreated catalyst for use in reactions such as a process for producing an oxirane by reacting an olefin and a peroxide compound in the presence of the pretreated catalyst. Even more specifically, the present invention relates to, for example, a process for epoxidizing allyl chloride to epichlorohydrin using the pretreated catalyst such as a pretreated titanium silicalite catalyst.

2. Description of Background and Related Art

The reaction of epoxidizing allyl chloride to epichlorohydrin using a titanium silicalite catalyst and hydrogen peroxide ($H_2O_2$) is a well known process such as disclosed in, for example, U.S. Pat. No. 7,323,578. To date, the known processes for epoxidizing allyl chloride to epichlorohydrin have not been commercialized.

It is also well known that methanol is a necessary reaction component of the process of epoxidizing allyl chloride to epichlorohydrin to obtain high activity with a titanium silicalite catalyst; and typically, in such known processes methanol is used in large excesses (50-90 weight percent) to ensure that the reaction mixture remains as one liquid phase. However, the use of a large excess of methanol results in the formation of byproducts from the reactions of methanol and water, which are solubilized in the organic phase by methanol, with epichlorohydrin. These large quantities of methanol also result in estimations of large towers and high energy consumption for predicted purification on a commercial scale.

In addition, problems of low olefin selectivity and of difficult separations exist in the known processes; however, such problems can be solved by reducing the methanol concentration or removing methanol entirely from the processes. Still, in the epoxidation of many olefins, reducing or eliminating methanol concentration in the known processes creates a reaction system with two liquid phases, which results in lower epoxide yield, lower $H_2O_2$ selectivity to epichlorohydrin, and/or longer reaction times.

Chinese Patent Application No. CN 200710039080.1 describes reaction conditions for epoxidizing allyl chloride to epichlorohydrin with titanium silicalite and $H_2O_2$ without the presence of any solvent, including methanol. The teachings of CN 200710039080.1 include a molar ratio of allyl chloride to $H_2O_2$ from 1-100:1, a weight ratio of $H_2O_2$ to catalyst from 0.2-200, reaction temperatures from 25-100° C., pressures from 0.1-0.2 MPa, and reaction times from 0.1-48 hours. The catalyst used is titanium silicalite and the ratio of $SiO_2/TiO_2$ is 10-200. The examples described in CN 200710039080.1 have $H_2O_2$ conversions greater than 95 percent (%) and $H_2O_2$ to epichlorohydrin selectivities greater than 92%. However, using commercially available titanium silicalite catalyst under the conditions given in CN 200710039080.1 results in a $H_2O_2$ to epichlorohydrin selectivity as low as 81%. CN 200710039080.1 mentions that its "solvent-less system" simplifies and reduces energy consumption in the separation and purification of the products, but CN 200710039080.1 does not provide any examples or evidence of energy reduction using its process.

SUMMARY OF THE INVENTION

The present invention is directed to a modified titanium silicalite-1 with MFI structure (TS-1) catalyst and to a process for making such modified catalyst.

In one embodiment, the present invention includes a modified TS-1 catalyst comprising a TS-1 catalyst which has been treated with methanol prior to the use of the catalyst. Optionally, the catalyst can further be filtered and/or air dried prior to the use of such modified catalyst. The TS-1 catalyst of the present invention is modified before the catalyst is used in a chemical reaction, resulting in activation of the TS-1 by the pretreatment with methanol. No additional solvent is necessary in the reaction composition, which promotes the formation of two liquid phases.

By pre-treating a TS-1 catalyst with methanol, then optionally, filtering the catalyst, and then optionally, air-drying the catalyst, a resulting pretreated activated catalyst can be obtained. This activated TS-1 may be used in an epoxidation reaction without adding methanol to the reaction mixture. The activated TS-1 catalyst of the present invention has a catalytic activity equivalent to known TS-1 catalysts that use large excesses of methanol during a reaction using the unmodified catalyst. By eliminating the need for additional methanol during the reaction, the losses of epichlorohydrin from solvolysis are minimized significantly by utilizing the pre-treated catalyst of the present invention. The present invention also solves the problem of costly separation units required to isolate epoxides from reactions carried out in the presence of 50 wt % or more of methanol.

In other embodiments, the pretreated catalyst of the present invention can also be used to epoxidize other olefins; or to oxidize aliphatic or aromatic hydrocarbons.

Another embodiment of the present invention is directed to a process for using the above catalyst in a chemical reaction process. For example, in a preferred embodiment, the catalyst of the present invention may be used in the epoxidation of allyl chloride to epichlorohydrin by hydrogen peroxide wherein the epoxidation is catalyzed by the TS-1 catalyst which has been activated by pretreatment with methanol in accordance with the present invention. The reaction is carried out in two liquid phases with no additional methanol added. The advantages that the system of the present invention offers are decreased losses of epichlorohydrin by solvolysis and decreased energy costs for separation, while maintaining fast reaction times.

The present invention is advantaged compared to those of the prior art which use 50 wt % or more methanol because the separation and isolation of the epoxide from the reaction mixture is facilitated. The removal of methanol as a solvent results in the formation of two liquid phases, which can be decanted after the reaction to obtain an epoxide-rich organic phase. The present invention process is advantaged compared to the prior art processes, for example as disclosed in CN 200710039080.1, because by pre-treating the catalyst with methanol and then using the modified catalyst of the present invention in a process, a higher selectivity of $H_2O_2$ to olefin, a higher olefin yield, and a higher selectivity of olefin versus byproducts can be achieved.

The present invention creates an advantage over conditions used in, for example, CN 200710039080.1, where no methanol is used, by increasing the yield for example by 10% or more, while decreasing the byproducts for example by over 50%. The present invention also presents an advantage over reactor compositions which use amounts of methanol of 50 wt % or higher as a solvent by decreasing by at least 80% the formation of chloromethoxypropanol, the main byproduct in these types of reactions.

Another advantage of the present invention is lower equipment cost and lower energy usage due to not having to separate out, recover and/or recycle methanol when used as a solvent in a reaction mixture.

BRIEF DESCRIPTION OF THE DRAWINGS

For the purpose of illustrating the present invention, the drawing shows a form of the present invention which is presently preferred. However, it should be understood that the present invention is not limited to the embodiments shown in the drawing.

FIG. 1 shows the derivative weight loss by thermogravimetric analysis (TGA) of a sample of activated TS-1 catalyst which has been pretreated with methanol in accordance with the present invention. FIG. 1 shows a first peak for the evolution of non-bound methanol present in the pores of the catalyst at approximately 60° C., and a second peak for the evolution of Ti-bound methanol at approximately 300-400° C.

DETAILED DESCRIPTION OF THE INVENTION

One broad embodiment of the present invention comprises an activated catalyst for use in chemical reactions, wherein the catalyst comprises a pre-treated catalyst which has been pretreated with methanol sufficiently to activate the catalyst. The pretreated catalyst may be filtered and air-dried resulting in a pretreated activated catalyst useful for various oxidation processes.

Another broad embodiment of the present invention includes a process for oxidizing olefins using the pretreated catalyst such as for example in the epoxidation of olefins to oxides.

The process for preparing an activated catalyst of the present invention comprises a pretreating titanium silicalite catalyst with MFI structure (TS-1 catalyst) with methanol. The pretreating step includes for example, the step of contacting TS-1 catalyst with methanol under conditions to have the methanol bond to the TS-1 catalyst prior to use of the catalyst.

The catalyst useful in the present invention includes known titanium silicalite catalyst structures. The TS-1 catalyst used in the present invention may be selected from commercially available catalysts such as TS-1 from SW Chemie, Polimeri Europa, or Clean Science, for example. Alternatively, the TS-1 catalyst can be manufactured by any of the known processes in the art such as those described in U.S. Pat. No. 4,410,501, for example.

In other embodiments of the present invention, other titanium silicates may be used such as titanium-silicalites with a MEL or intermediate MFI/MEL structure and titanium-silicalites from beta zeolites containing titanium and having a BEA structure. Other titanium containing zeolite catalysts generally known as TS-2, TS-3, Ti-MCM-22, Ti-MWW, ZSM-48 and ZMS-12 can also be used for preparing the catalyst of the present invention.

The concentration of the TS-1 catalyst used in the present invention is generally from about 0.1 weight percent (wt %) to about 50 wt %; preferably from about 0.1 wt % to about 25 wt %; and more preferably from about 1 wt % to about 10 wt %.

The methanol useful in the present invention includes known methanol compounds commercially available such as methanol from Fisher Scientific.

The amount of methanol (MeOH) used to pretreat the TS-1 catalyst is generally at a mole ratio of MeOH to TS-1 catalyst of from about 0.1:1 MeOH:TS-1 to about 100:1 MeOH:TS-1; preferably, from about 1:1 MeOH:TS-1 to about 100:1 MeOH:TS-1; more preferably, from about 1:1 MeOH:TS-1 to about 50:1 MeOH:TS-1; and most preferably, from about 5:1 MeOH:TS-1 to about 10:1 MeOH:TS-1.

The fraction (the at least a portion) of titanium that is chemically bonded with methanol in TS-1 catalyst generally is from about 50% to about 200%, preferably from about 100% to about 200%, and more preferably from about 150% to about 200%; as determined by infrared (IR) spectroscopy and TGA; and based on the theory that each Ti molecule can bind two MeOH molecules.

Generally, the process of pretreating the catalyst includes for example contacting a TS-1 catalyst with the methanol at a temperature of from about −20° C. to about 60° C., preferably from about 0° C. to about 60° C., and more preferably from about 25° C. to about 60° C. The contacting step may be carried out by known methods and equipment such as mechanical stirring, flowing through a packed catalyst bed, or soaking in a container; and the like.

The contacting step can be carried out for a pre-determined period of time sufficient to bond the methanol to the TS-1 catalyst, such as for example, generally for about 1 minute to about 24 hours, preferably from about 5 minutes to about 1 hour, and more preferably from about 30 minutes to about 1 hour.

After the contacting step, the pretreated catalyst may be separated from the excess methanol from the catalyst. Any separation method known in the art may be used such as filtering, centrifuging, evaporating, decantation, and the like.

Optionally, the isolated pretreated catalyst may be dried before or after filtering the catalyst. Any drying method known in the art may be used to dry the catalyst such as by flowing air, placement in a dessicator, or placement in an oven at temperatures below about 65° C. with or without the presence of air.

After isolating the pretreated catalyst, the pretreated catalyst may be used in various chemical reaction processes such as epoxidations, hydroxylations, or other oxidation reactions.

As aforementioned, the pretreated catalyst product of the present invention preferably contains at least a portion of methanol chemically bonded to titanium atoms of the catalyst. The fraction of titanium that is chemically bonded with methanol in TS-1 catalyst generally is from about 50% to about 200%, preferably from about 100% to about 200% and more preferably from about 150% to about 200%; as determined by IR spectroscopy at a frequency of 950-970 $cm^{-1}$, depending on the TS-1 catalyst crystal size; and based on the theory that each Ti molecule can bind two methanol molecules.

The chemisorption of MeOH onto Ti causes a shift in the frequency of the Ti—O stretch to higher wavenumbers. The chemisorption is also evidenced by evolution of material in a TGA at approximately 400° C. Optionally, there may be methanol that is not chemically bonded but may be retained and present in the pores of the catalyst as well. This is not seen in the IR spectrum at the indicated range, and evolves at approximately 65° C. in the TGA.

For example, a sample of TS-1 catalyst with a crystal size of approximately 0.1-0.3 μm was pretreated with methanol at room temperature for 1 hour, and then filtered and air-dried. The non-activated catalyst had a peak at 963.6 cm$^{-1}$, which shifted to 968.0 cm$^{-1}$ upon chemisorption of methanol. As shown in FIG. 1, TGA of an activated methanol-pretreated catalyst shows the evolution of non-bound methanol in the pores of the catalyst at approximately 60° C., and the evolution of Ti-bound methanol at approximately 300-400° C.

The pretreated catalyst of the present invention may be used in a process for oxidizing an olefin including reacting an olefin with an oxidant in the presence of the pretreated catalyst and under reaction conditions to prepare an epoxide; wherein the oxidizing reaction (also referred to herein as an epoxidation reaction) is catalyzed by the methanol pretreated TS-1 catalyst of the present invention which has been activated by pretreatment with methanol as described above.

As an illustration of one embodiment of the use of the pretreated catalyst of the present invention, the pretreated catalyst may be used in a process for preparing epichlorohydrin by epoxidizing allyl chloride with hydrogen peroxide in the presence of the activated methanol pretreated TS-1 catalyst of the present invention.

The reaction mixture including an olefin comprises a multiple liquid phase composition useful for preparing an oxirane product. The olefin used in the reaction mixture includes, for example: (a) at least one olefin; wherein the olefin is selected from one of (i) an aliphatic olefin or substituted aliphatic olefin, with the proviso that the aliphatic olefin is not propylene, (ii) a cycloaliphatic olefin, (iii) an aromatic olefin, (iv) a cycloaromatic olefin, and (v) mixtures thereof.

Embodiments of the olefin used in the epoxidation reaction of the present invention may include for example chloride-butadiene and other linear dialkenes; cyclohexene and other cyclic alkenes and dialkenes; substituted alkenes, such as halogenated alkenes, styrene, divinylbenzene, dicyclopentadiene; other aromatic alkenes; and mixtures thereof. Moreover, butenes, pentenes, hexenes, octeneheptenes-1, 1-tridecene, mesityl oxide, isoprene, cyclo-octane, cyclohexene or bicyclic compounds such as norbornenes or pinenes may also be used in the process. In a preferred embodiment, the olefin used in the present invention is ally chloride.

The allyl chloride useful in the epoxidation process of the present invention includes known allyl chloride compounds. Alternatively, the allyl chloride can be manufactured by known processes such as thermochlorination.

The concentration of the allyl chloride used in the epoxidation process is generally from about 10 wt % to about 90 wt %, preferably from about 20 wt % to about 80 wt %, and more preferably from about 30 wt % to about 70 wt %.

The oxidant useful in the epoxidation process of the present invention includes known oxidant compounds such as peroxocompounds such as a hydroperoxide including for example hydrogen peroxide, commercially available from Fisher Scientific. Examples of other hydroperoxides that may be used include, but are not limited to, tert-butyl hydroperoxide, ethylbenzene hydroperoxide, acetyl peroxide, benzoyl peroxide, methyl ethyl ketone peroxide, cumene peroxide, and combinations thereof.

In one embodiment of the present invention, the epoxidation of allyl chloride may be carried out preferably using hydrogen peroxide. An advantage of this process is the avoidance of forming by-products and/or co-products.

The concentration of the oxidant used in the epoxidation process is generally from about 1 wt % to about 30 wt %, preferably from about 1 wt % to about 15 wt %, and more preferably from about 1 wt % to about 7 wt %.

Generally, the epoxidation process of the olefin includes for example mixing the olefin with an oxidant at a temperature of from about 0° C. to about 60° C., preferably from about 10° C. to about 50° C., and more preferably from about 25° C. to about 45° C. The mixing step may be carried out by known methods and equipment such as a stirred batch reactor, a plug flow reactor, a continuously stirred tank reactor, a fluidized bed reactor, a loop reactor, or a tubular reactor, and the like.

After the above mixing step, the resultant epoxy may be recovered from the reaction mixture. Any recovery method known in the art may be used such as decantation, extraction, evaporation, or distillation, and the like.

After isolating the epoxide, the epoxide may be further used as an intermediate product in various processes such as for making coatings and composites.

In the process of producing an epichlorohydrin from allyl chloride, the process steps may include the following steps: addition of reactants, mixing the reactants in the presence of a catalyst, separation of the reactants from the catalyst, separation of epichlorohydrin from the reaction mixture, and optionally recycle of unreacted allyl chloride and/or solvents.

Some of the advantages of the process of the present invention include for example, (1) no methanol is needed or used to prepare an epoxide product, for example in the process of producing epi, the use of no methanol facilitates separation and isolation of the desired epichlorohydrin product; (2) an increase in yield of epoxide product, for example in the process of producing epichlorohydrin, the epi yield is preserved, while the losses of epichlorohydrin to byproducts is reduced; (3) a decrease in methanol byproducts production, thus providing a purer epoxide product; and (4) lower equipment cost and lower energy usage due to not having to separate out, recover and/or recycle methanol when used as a solvent in a reaction mixture.

EXAMPLES

The following examples and comparative examples further illustrate the present invention in detail but are not to be construed to limit the scope thereof. Unless otherwise indicated, all parts and percentages are by weight. Unless otherwise specified, all instruments and chemicals used are commercially available.

In the following Examples, various terms and designations are used such as for example, "GC" stands for gas chromatography; "epi" stands for epichlorohydrin; "biphasic" means two liquid phases which are present in addition to any solid or gas phases which may be present in a reaction mixture.

In the following Examples, standard analytical equipment and methods are used including the following:

Gas chromatography (GC) was performed on an HP 6890 series G1530A GC with a JP 7682 series injector and flame ionization detector.

The amount of hydrogen peroxide was analyzed by iodometric titration using 0.01 normality (N) sodium thiosulfate. The hydrogen peroxide concentration was calculated as follows: parts per million (ppm) hydrogen peroxide=(milliliter (ml) titrant used) (0.01N) (17000)/g sample. Titrations were performed using a Mettler Toledo DLSx V2.3 titrator with a DM140 sensor.

Example 1

Part A.—Pretreatment of the TS-1 Catalyst

TS-1 catalyst (6.90 g) was stirred with MeOH (50 mL) at 25° C. for 1 hour. The catalyst was vacuum filtered through a 0.45 μm filter paper and air-dried in a desicator. The resulting TS-1 catalyst prepared this way will hereafter be referred to as the "pretreated TS-1 catalyst."

Part B.—Epoxidation Process using the Pretreated TS-1 Catalyst

Allyl chloride (363.10 g, high purity, 99.6%, obtained from The Dow Chemical Company and pretreated TS-1 catalyst (7.173 g, Si/Ti=~30) prepared in Part A. above were added to a 750-mL jacketed glass reactor with a stainless steel cooling coil, thermocouple, mechanical stirrer, addition funnel, $N_2$ purge with gas scrubber, and reflux condenser/cold finger combination. 32 wt %/aqueous (aq.) hydrogen peroxide (80.02 g) was charged to the addition funnel, and then added to the reactor slowly after the allyl chloride/catalyst mixture was brought to 25.5° C. The mixture was stirred at 600 rpm, and the reaction was maintained at approximately 25° C. using the cooling coil.

After 300 minutes, the reactor contents of the reactor were drained equally into two 250 mL centrifuge tubes, and then centrifuged at 3000 rpm and 0° C. for 30 minutes. The liquid was decanted from the catalyst into a separatory funnel, where resultant organic and aqueous phases were collected separately.

Both the organic and aqueous phases were analyzed by GC; and the amount of peroxide remaining was determined by titration with sodium thiosulfate. The results of this Example 1 are reported in Table I.

Comparative Example A

Methanol Solvent/Single Phase Reaction Conditions

Allyl chloride (115.30 g, high purity, 99.6%, obtained from The Dow Chemical Company, TS-1 catalyst (6.900 g, Si/Ti~30), and methanol (201.25 g), were added to a 750-mL jacketed glass reactor with a stainless steel cooling coil, thermocouple, mechanical stirrer, addition funnel, $N_2$ purge with gas scrubber, and reflux condenser/cold finger combination. 32 wt %/aq. hydrogen peroxide (80.01 g) was charged to the addition funnel, and then added to the reactor slowly after the allyl chloride/catalyst/methanol mixture was brought to approximately 25° C. The mixture was stirred at 600 rpm, and the reaction was brought up to 40° C. by the reaction exotherm and maintained at approximately 40° C. using the cooling coil.

Samples of the reaction mixture were filtered using a 0.45 μm syringe filter to remove any catalyst particles, and then analyzed by GC.

When the reaction was deemed complete by epi analysis via GC (after 75 minutes), the reactor contents were drained equally into two 250 mL centrifuge tubes, and then centrifuged at 3000 rpm and 0° C. for 30 minutes. The liquid was decanted from the catalyst and analyzed by GC and the amount of peroxide remaining was determined by titration with sodium thiosulfate. The results of this Comparative Example A are reported in Table I.

Example 2

Part A.—Pretreatment of the TS-1 Catalyst

TS-1 catalyst (6.6469 g, Si/Ti=~30) was stirred with MeOH (50 mL) at 25° C. for 1 hour. The catalyst was vacuum filtered through a 0.45 μm filter paper and air-dried in a dessicator resulting in a modified catalyst (hereafter "pretreated TS-1 catalyst").

Part B.—Epoxidation Process using the Pretreated TS-1 Catalyst

Allyl chloride (268.9 g, high purity, 99.6%, obtained from The Dow Chemical Company and all of the pretreated TS-1 catalyst prepared in Part A. above were added to a 750-mL jacketed glass reactor with a stainless steel cooling coil, thermocouple, mechanical stirrer, addition funnel, $N_2$ purge with gas scrubber, and reflux condenser/cold finger combination. 30 wt %/aq. hydrogen peroxide (39.88 g) was charged to the addition funnel, and then added to the reactor slowly after the allyl chloride/catalyst mixture was brought to about 25° C. The mixture was stirred at 600 rpm, and the reaction was brought up to 40° C. by the reaction exotherm and maintained at about 40° C. using the cooling coil.

After 60 minutes, the reactor contents were drained equally into two 250 mL centrifuge tubes, and then centrifuged at 3000 rpm and 0° C. for 30 minutes. The liquid was decanted from the catalyst into a separatory funnel, where resultant organic and aqueous phases were collected separately.

Both the organic and aqueous phases were analyzed by GC; and the amount of peroxide remaining was determined by titration with sodium thiosulfate. The results of this Example 2 are reported in Table I.

Comparative Example B

Biphasic Reaction Conditions

In this Comparative Example B, a biphasic reaction was carried out where no MeOH is added as a solvent, and the catalyst was not pretreated. The conditions in this Comparative Example B are similar to the conditions reported in Chinese Patent Application No. CN 200710039080.1, except that the TS-1 catalyst used in this Comparative Example B was purchased from Süd Chemie.

In carrying out this Comparative Example B, allyl chloride (400.62 g, epi grade, 99.4%, obtained from The Dow Chemical Company) and TS-1 catalyst (10.0518 g, Si/Ti=~30) were added to a 750-mL jacketed glass reactor with a stainless steel cooling coil, thermocouple, mechanical stirrer, addition funnel, $N_2$ purge with gas scrubber, and reflux condenser/cold finger combination. 30 wt %/aq. hydrogen peroxide (60.01 g) was charged to the addition funnel, and then added to the reactor slowly after the allyl chloride/catalyst mixture was brought to approximately 25° C. The mixture was stirred at 600 rpm, and the reaction was brought up to 40° C. by the reaction exotherm and maintained at approximately 40° C. using the cooling coil.

After 60 minutes, the reactor contents were drained equally into two 250 mL centrifuge tubes, and then centrifuged at 3000 rpm and 0° C. for 30 minutes. The liquid was decanted from the catalyst into a separatory funnel, where the organic and aqueous phases were collected separately. Both phases were analyzed by GC; and the amount of peroxide remaining was determined by titration with sodium thiosulfate. The results of Comparative Example B are reported in Table I.

TABLE I

| EXAMPLE | TS-1 (wt %) | H$_2$O$_2$ (wt %) | Allyl (wt %) | MeOH (wt %) | T (° C.) | Reaction Time (minutes) | Yield | H$_2$O$_2$ Selectivity | CMP/epi (wt/wt) | MCH/epi (wt/wt) |
|---|---|---|---|---|---|---|---|---|---|---|
| Example 1 | 1.5% | 5.7% | 80.7% | 0% - p.t | 25 | 300 | 89.2% | 89.8% | 0.004 | 0.011 |
| Comp. Ex. A | 1.7% | 6.3% | 28.5% | 49.9% | 40 | 75 | 92.1% | 97.8% | 0.020 | 0.004 |
| Example 2 | 2.1% | 3.8% | 85.1% | 0% - p.t | 40 | 60 | 84.2% | 84.8% | 0.006 | 0.025 |
| Comp. Ex. B. | 2.1% | 3.8% | 85.1% | 0.0% | 40 | 60 | 76.3% | 80.7% | 0.000 | 0.071 |

Footnotes for Table I:
"Yield" = (amount of epi produced)/(maximum amount of epi at full H$_2$O$_2$ conversion);
"0% - p.t." = catalyst was pretreated with methanol in accordance with the invention and no further methanol was added;
"CMP" = 1-chloro-3-methoxy-2-propanol;
"MCH" = 1-chloro-2,3-propanediol (monochlorohydrin); and
"epi" = epichlorohydrin.

The present invention is advantaged over prior art such as those conditions used in Comparative Example A because the epichlorohydrin yield is preserved, while the losses of epichlorohydrin to byproducts is reduced. The present invention is further advantaged because it does not require the use of amounts of methanol of 50 wt % or more, which facilitates separation and isolation of the desired epichlorohydrin product.

The present invention is advantaged over prior art such as those conditions used in Comparative Example B and Chinese Patent Application No. CN 200710039080.1 because the present invention provides an increase in epichlorohydrin yield by almost 10%, while the epichlorohydrin losses to byproducts are reduced by over 50%.

While the present disclosure includes a limited number of embodiments, the scope of the present invention should be limited only by the attached claims and not by the embodiments herein as other embodiments are possible to those skilled in the art having benefit of this disclosure.

What is claimed is:

1. A multiple liquid phase composition, useful for preparing an oxirane product, comprising a reaction mixture of: (a) at least one olefin; wherein the olefin is selected from one of (i) an aliphatic olefin or substituted aliphatic olefin, with the proviso that the aliphatic olefin is not propylene, (ii) a cycloaliphatic olefin, (iii) an aromatic olefin and mixtures thereof; (b) at least one peroxide compound; and (c) a titanium silicalite catalyst with MFI structure (TS-1 catalyst) pretreated with methanol at a mole ratio of methanol to TS-1 catalyst from 0.1:1 methanol:TS-1 catalyst to 100:1 methanol:TS-1 catalyst at a temperature of from about −20° C. to about 60° C. for about 1 minute to about 24 hours and air-dried such that at least a portion of the methanol is chemically bound to the activated catalyst and a portion of the methanol is not chemically bound to the activated catalyst; and wherein the fraction of titanium that is chemically bonded with methanol in the activated catalyst comprises from 50% to 200% as determined by IR spectroscopy at a frequency of 950-970 cm$^{-1}$.

2. The composition of claim 1, wherein the at least one olefin comprises allyl chloride; and the at least one oxirane product comprises epichlorohydrin.

3. The composition of claim 1, wherein the at least one peroxide compound comprises hydrogen peroxide.

4. The composition of claim 1, wherein the titanium silicalite catalyst is in the form of a solid activated catalyst and wherein said catalyst maintains its reactivity in the epoxidation reaction.

* * * * *